US005279576A

United States Patent [19]

Loo et al.

[11] Patent Number: 5,279,576

[45] Date of Patent: Jan. 18, 1994

[54] MEDICATION VIAL ADAPTER

[76] Inventors: George Loo, 9814 Curwood Pl., Beverly Hills, Calif. 90210; Edward Thibon, 99 W. Sandra Ave., Arcadia, Calif. 91006

[21] Appl. No.: 888,740

[22] Filed: May 26, 1992

[51] Int. Cl.[5] .................. A61M 5/00

[52] U.S. Cl. .................. 604/187; 604/414; 604/411; 222/1

[58] Field of Search .................. 604/403, 411, 414, 905, 604/415, 416, 187; 222/1, 82, 209, 420

[56] References Cited

U.S. PATENT DOCUMENTS

| | | | |
|---|---|---|---|
| 3,098,481 | 7/1963 | Wikander | 604/411 |
| 3,940,003 | 2/1976 | Larson | 604/411 |
| 4,230,112 | 10/1980 | Smith . | |
| 4,505,709 | 3/1985 | Froning | 604/411 |
| 4,568,346 | 2/1986 | van Dijk | 604/414 |
| 4,650,475 | 3/1987 | Smith et al. . | |
| 4,759,756 | 7/1988 | Forman et al. . | |
| 4,808,381 | 2/1989 | McGregor et al. | 604/411 |
| 4,834,149 | 5/1989 | Fournier et al. | 604/411 |
| 4,883,483 | 11/1989 | Lindmayer | 604/411 |
| 4,913,699 | 4/1990 | Parsons . | |
| 4,944,736 | 7/1990 | Holtz | 604/411 |
| 4,969,883 | 11/1990 | Gilbert et al. . | |
| 5,035,689 | 7/1991 | Schroeder . | |
| 5,163,583 | 11/1992 | Whitworth | 604/411 |

OTHER PUBLICATIONS

Advertisement from Burron Medical Inc. on their transfer devices, acknowledged to be prior art.

*Primary Examiner*—C. Fred Rosenbaum
*Assistant Examiner*—Chalin Smith
*Attorney, Agent, or Firm*—Limbach & Limbach

[57] ABSTRACT

An adapter for interfacing a needle-less syringe with a medication vial is disclosed. The adapter has a body and a detachable means for sealably receiving the inlet of the syringe at one end. The detachable means is substantially centered about the body and has a central bore fluidically connecting the adapter with the syringe. Extending substantially perpendicular to the body and opposite to the detachable means is a piercing means which is substantially elongated in shape. The piercing means has a longitudinal axis with a spike bore extending along the longitudinal axis fluidically connecting the central bore with the spike bore. An adapter inlet is positioned along the longitudinal axis fluidically connecting to the spike bore, at a distance such that the distance between the inlet and the body is greater than the thickness of the cap of the medicine vial. At least two resilient permanent attachment means extend from the body substantially in the same direction as the piercing means with each limb having a length less than that of the piercing means. Angled foot members are attached to the distal ends of each of the limbs with each of the foot members having guide means extending inward and upward from the limb towards the piercing means, and permanent attachment hook means on the end opposite the guide means.

4 Claims, 4 Drawing Sheets

MEDICATION VIAL ADAPTER

TECHNICAL FIELD

The present invention relates to an adapter which locks onto a medication vial (MV) and provides an interface between the medication vial (MV) and a needle-less syringe to permit filling the syringe with medication inside of the MV without the use of a needle.

BACKGROUND OF THE INVENTION

With the increased concern about the possibility of contracting blood borne diseases, such as AIDS and hepatitis, from accidental, self-inflicted, needle stick injuries with a possibly contaminated needle, the health care industry is presently concentrating on minimizing, or eliminating, the use of needles wherever possible. The FDA has urged health care workers to avoid re-capping of needles after using them for intravenous (IV) and intramuscular injections. One solution to avoiding re-capping needles after using them for IV injections is to use a needle-less IV injection port. The use of needle-less IV injection ports has become more widespread over the past few years. One complaint, however, when using a needle-less IV injection port is that one must still use a needle to fill the syringe, before it can be used with the needle-less IV injection port. A needle used to fill a syringe is usually not infectious, but the use of a needle here, does expose a health care worker to a potential needle stick, and does add the extra cost of a needle. One way to avoid this potential needle-stick, and fill a syringe without the use of a needle, is to use a medication vial (MV) adapter.

There are a few special devices presently described which do permit filling syringes without the use of needles (Froning et al., U.S. Pat. No. 4,505,709, Smith et al., No. 4,650,475, and Schroeder, No. 5,035,689). There are some devices that have means for affixing themselves to a medication vial (Forman et al., No. 4,759,756, Gilbert et al., No. 4,969,883, and Holtz, No. 4,944,736). These devices and the methods used to attach them to a standard MV (Holtz, Froning et al., Smith et al., Forman et al., Schroeder) are somewhat cumbersome. Their design makes them hard to attach their respective device to the MV, and this difficulty in attaching them to the MV can easily lead to contamination of the device, with loss of sterility of the device, loss of sterility of the MV, and loss of sterility of the medication contained inside of the MV.

Other examples of related art in this field are shown in Smith, U.S. Pat. No. 4,230,112, Parsons, U.S. Pat. No. 4,913,699, and Curley et al., U.S. Pat. No. 4,328,802.

SUMMARY OF THE INVENTION

The present invention is an improved medication vial (MV) adapter that locks onto a standard MV at one end, and interfaces with a standard needle-less syringe at the opposite end, to permit filling a syringe with medication, without the use of a needle, in a more sterile, and more efficient manner. The adapter has a body with a detachable means on one end, and a locking and piercing means on the opposite end. The detachable means is for sealably connecting to the inlet of a needle-less syringe and is centered substantially on the body, and has a central bore which fluidically connects the adapter with the syringe. The piercing means, for piercing the cap of the medication vial, is substantially elongated in shape and has a longitudinal axis with a spike bore extending along the longitudinal axis, fluidically connecting the central bore to the spike bore. An adapter inlet is positioned along the longitudinal axis at a distance such that the distance between the inlet and the body is only slightly greater than the thickness of the cap of the medication vial. At least two resilient locking attachment limbs extend from the body substantially in the same direction as the piercing means with each limb having a length substantially less than that of the piercing means. Angled foot pieces are attached to the distal ends of each of the resilient limbs. Each of the angled foot pieces has an inward and upward extending guiding ramp portion on the outer, lower end, and a hook portion on the opposite, inner, upper end.

DETAILED DESCRIPTION OF THE PREFERRED EMBODIMENTS

Figure 1:
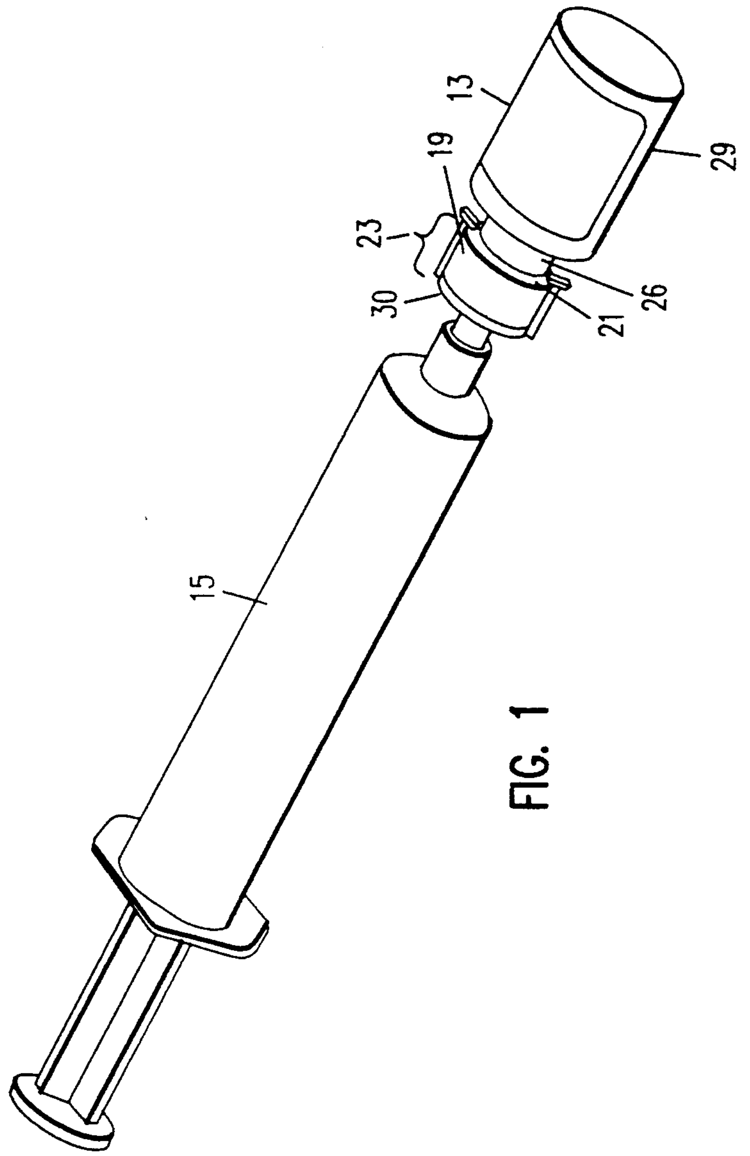
FIG. 1 is an oblique view of one embodiment of the invention with a standard type syringe attached to the outlet end, and a standard type medication vial (MV) attached to the inlet end. The MV is affixed to the improved MV adapter of the present invention by a spike end and resilient attachment means.
Figure 2:
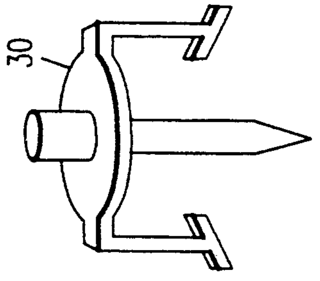
FIG. 2 is an oblique view of one embodiment of the MV adapter of the present invention.
Figure 5:
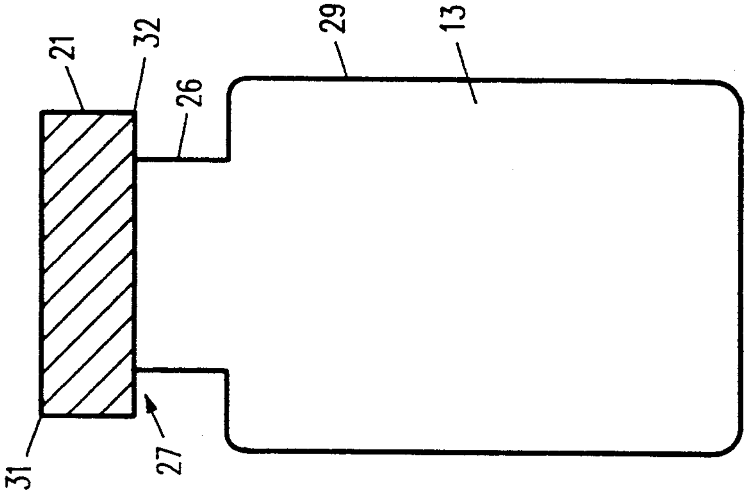
FIG. 5 is a side view of a fully assembled prior art standard MV with the metal band affixing the rubber sealing stopper onto the glass mouth of the MV, showing the neck and cylindrical body portions of the MV.
Figure 6:
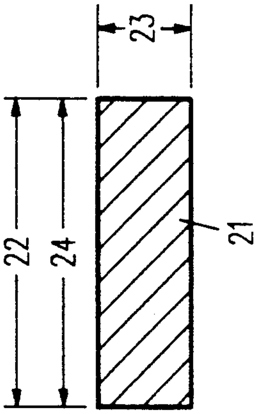
FIG. 6 is a side view of the prior art metal band as it appears after it has been placed over the rubber sealing stopper and the glass mouth of the standard MV, and has been crimped over the lower edge of the glass mouth to affix the rubber sealing stopper onto the MV and form a hermetic seal.
Figure 4:
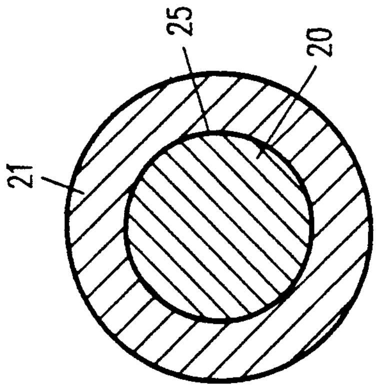
FIG. 4 is a top view of the prior art fully assembled top of a standard MV showing the exposed portion of the rubber sealing stopper as accessed through the opening in the metal band.
Figure 3:
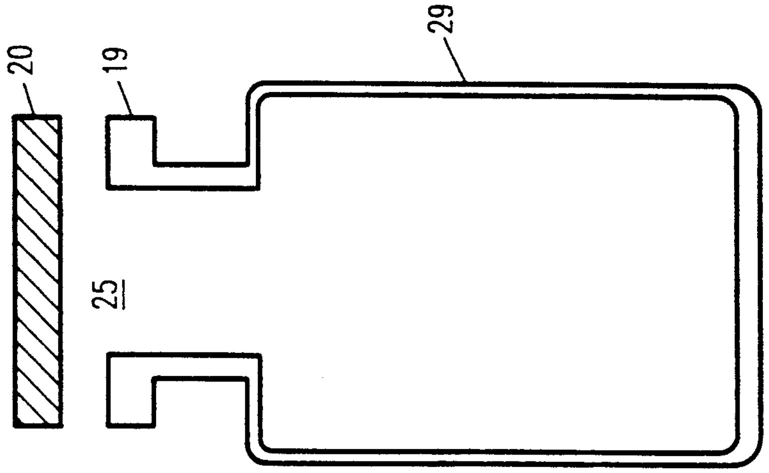
FIG. 3 is a cross-sectional view of the prior art unassembled standard MV showing the rubber sealing stopper fitting over the mouth of the standard MV, after the MV has been filled with medication, and before the rubber sealing stopper has been permanently attached to the glass vial by a crimped metal band.
Figure 9:
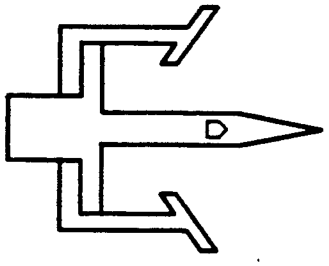
FIG. 9 is a side view of another embodiment of the invention, showing the device built as two mating components which functions similar to the embodiments built as one unit.
Figure 8:
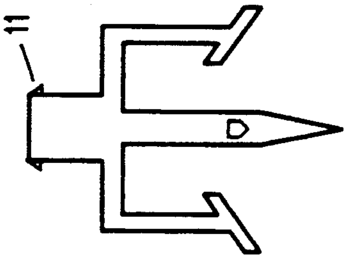
FIG. 8 is a side view of another embodiment of the invention, showing the presence of standard, prior art, luer locking lugs on the syringe end.
Figure 10:
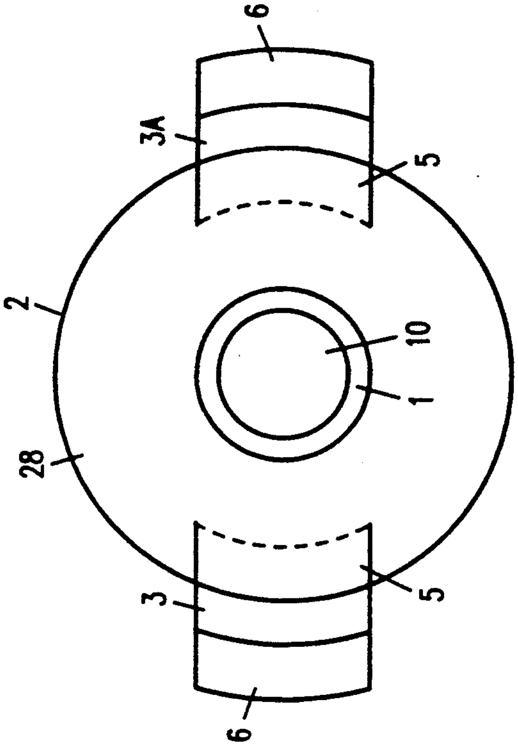
FIG. 10 is a top view of the invention without the sterile, reusable cover cap, showing the flow channel in the syringe end, and a top view of the resilient attachment means.
Figure 7:
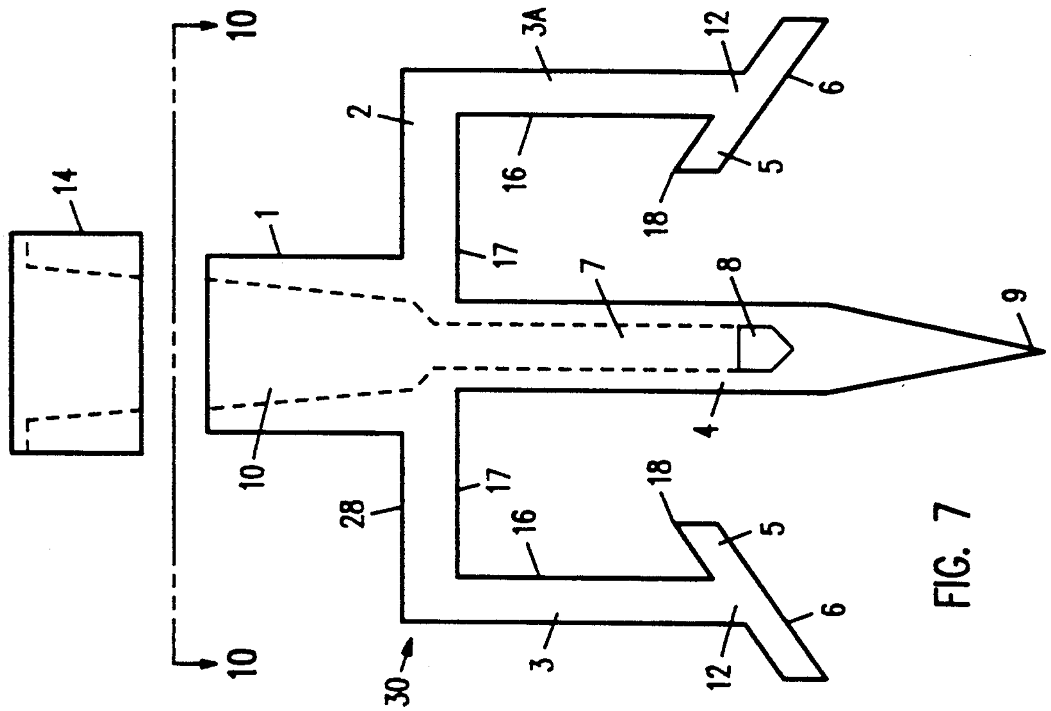
FIG. 7 is a side view of one embodiment of the invention, showing the reusable sterile cover cap and the medication flow path through the syringe end, the flange, the spike end, and the fluid entry side hole, or side holes, in the spike end.
Figure 11:
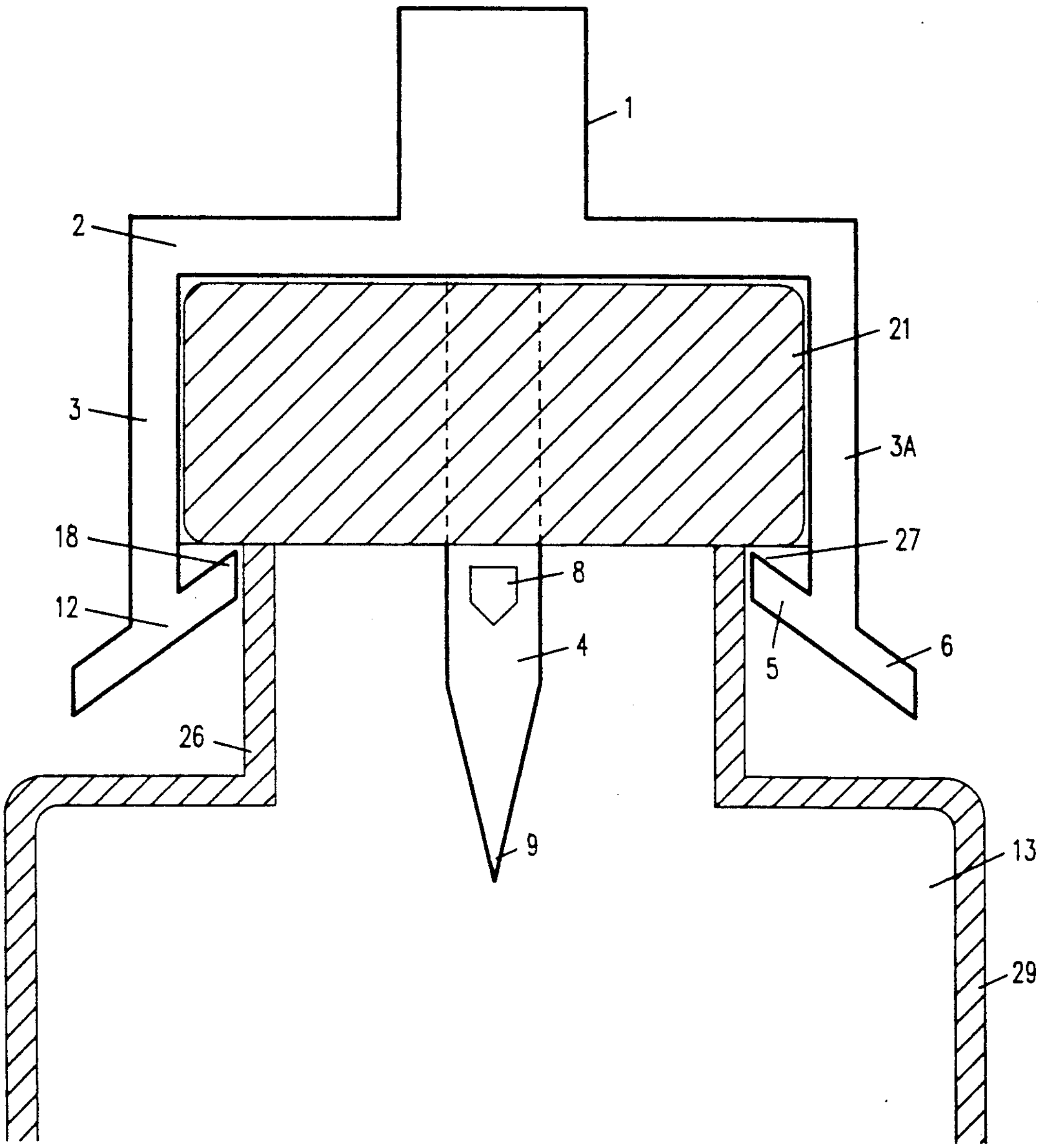
FIG. 11 is a side view of one embodiment of the invention showing its locked-on position when affixed to the standard medication vial.

The reference numbers used in the descriptions that follow refer to features of the invention shown in FIGS. 1 through 11.

The present invention of "an improved medication vial adapter" is used with a hermetically sealed medication vial (MV) 13 of standard type and shape. The MV 13 is typically made of transparent glass or plastic, and includes a mouth 19 with a stopper 20 of rubber or elastomer type material mounted thereupon by metal band 21. The glass mouth 19 of the MV 13 narrows down to a neck 26 and then broadens out again to a cylindrical part 29 which contains the sterile medication. A metal band 21 is mounted about the mouth 19, retaining the rubber or elastomer stopper 20 to the top of the MV 13 and forms part of the top cover of the MV 13. The metal band 21 has a central opening 25 on its top surface which exposes the access site of the rubber or elastomer stopper 20 as it is bound by the metal band 21 to the glass mouth for piercing. The center of the rubber or elastomer stopper 20 exposed in the center opening 25 of metal band 21 serves as an access site to the sterile medication contained inside the MV.

A junction 27 is formed where the edge of the metal band 21 is crimped, and meets the glass of the bottom side of the mouth 19 near the neck 26 of the MV. The rubber or elastomer stopper 20 is self-sealing when a piercing device has been inserted through it and also when the piercing device is removed from it, provided that the diameter of the piercing device was not too large. In addition the metal band 21 affixing the rubber or elastomer stopper 20 to the mouth 19 has a height or thickness 23.

The improved medication vial adapter of the present invention 30 consists of a syringe attaching end 1, a flange 2, at least two resilient attachment limbs 3 and 3*a*, and a piercing spike end 4 with a central bore 7. Syringe attaching end 1 has a central bore 10, which extends through the flange 2, and communicates with the central bore 7 of the piercing spike end 4.

Syringe end 1 may or may not contain luer locking lugs 11 (shown in FIG. 8) depending on which embodiment is presented. When not being used, syringe end 1 is covered with a removable and re-usable sterile hermetic sealing cover cap 14. Cover cap 14 preserves sterility of the syringe end 1 and the medication contained within the attached standard MV 13. Cover cap 14 also prevents leakage of medication from inside of the standard MV 13 when the standard MV 13 is placed on its side with the improved MV adapter 30 of the present invention attached.

The spike end 4 has a sharp pointed tip 9, a central bore 7, and a fluid entry side hole, or side holes 8, depending upon which embodiment of the improved MV adapter 20 of the present invention is presented.

The two resilient attachment limbs 3 and 3*a* of the improved MV adapter 30 of the present invention are similar in design, but are set on flange 2 as mirror images of each other. The free ends of resilient attachment limbs 3 and 3*a* terminate in an angled foot piece 12. Each angled foot piece 12 of the improved MV adapter 30 of the present invention is angled upward, and points inward, like sides of an inverted funnel, and has a hook portion 5 on the inner, upper end, and a guiding ramp portion 6 on the outer, lower, end.

The distance between the resilient attachment limbs 3 and 3*a* of the improved MV adapter 30 of the present invention is substantially equal to the diameter 22 of the metal top 21 of the standard medication vial 13. The vertical distance between the lower side 17 of the flange 2 and the upper tip 18 of hook portion 5, of angled foot piece 12, of resilient attachment limbs 3 and 3*a* of the improved MV adapter 30 of the present invention, in closest proximity to the lower side 17 of flange 2, is equal to the height 23 of the metal top 21 of the standard medication vial 13.

The piercing spike end 4 of the improved MV adapter 30 of the present invention is formed in the radial center of the lower side 17 of the flange 2. The hollow syringe end 1 of the improved MV adapter 30 of the present invention is formed at the radial center of the top surface 28 of the flange 2 opposite the spike end 4. There is a central fluid flow channel 7 which begins in the spike end 4 at fluid entry side hole (or holes) 8 and passes through the radial center of flange 2, to communicate with the central flow channel 10 in syringe end 1.

The opening hole (or holes) 8 of the medication fluid flow channel 7 in the spike end 4 of the improved MV adapter 30 of the present invention is placed at the level where the maximum amount of medication can be removed from the standard medication vial 13 when the improved MV adapter 30 is attached to the standard MV 13 by the attachment means 3 and 3*a*. Thus, the distance between the opening hole (or holes) 8 of the flow channel 7 in the spike end 4 and the lower side 17 of flange 2 of the improved MV adapter 30 of the present invention is greater than the combined thickness of the rubber or elastomer stopper 20 and the thickness of the top wall of the metal top 21. In the preferred embodiment, the distance is only slightly greater. The diameter of the bore of the central flow channel 7 through 10 varies dependent upon the diameter of the part of the improved MV adapter 30 of the present invention that it is passing through, so that the bore is always maximum to give the best combination of maximum fluid flow rate and tubular wall strength.

The syringe attaching end 1 of the improved MV adapter of the present invention 30 may or may not contain luer locking lugs 11. In the preferred embodiment of the improved MV adapter 30 the luer locking lugs 11 are absent. Absence of the luer locking lugs 11 makes using the improved MV adapter 30 faster and more efficient. Without the presence of luer locking lugs 11, needle-less syringes 15 can be quickly pushed onto, and pulled off of, the syringe end 1 as they are being filled with medication without the use of a needle. With the absence of the luer locking lugs 11, it is not necessary to use the more time consuming, less efficient, method of screwing and locking the empty syringe 15 onto, and then unscrewing and unlocking the medication filled syringe 15 from the attaching end 1 of the improved MV adapter 30 of the present invention.

The flange 2 of the improved MV adapter 30 is disk shaped. With the resilient attachment means 3 and 3*a*, the improved MV adapter 30 of the present invention may be made as one piece or as two separate mating pieces. Whether it is made as one piece, or two separate mating pieces, the improved MV adapter 30 will function the same. Once the improved MV adapter 30 has been affixed to the standard MV 13, the flange 2 protectively shields the top of the standard MV 13 from any spilled liquids and particulate matter falling onto the flange 2. In this manner, flange 2 helps maintain sterility of the medication inside of the MV 13. The removable and re-usable cover cap 14 forms a hermetic seal with, and protects the syringe end 1 of the improved MV adapter 30 and the MV contents from contamination of sterility. When filling a syringe 15, the re-usable cap 14 is removed and laid aside in a sterile manner. When the syringe 15 has been filled and removed from the improved MV adapter 30, the cover cap 14 is replaced over the syringe end in a sterile manner.

The distance between the two upper tips 18 of hook portions 5 of the angled foot pieces 12 of the resilient attachment limbs 3 and 3*a* of the improved MV adapter 30 of the present invention is shorter than the diameter 22 of the metal top 21 and is equal to or slightly shorter than the diameter across the glass neck 26. The space enclosed by the lower edges 17 of the flange 2, the inner facing edges 16 of the resilient attachment limbs 3 and 3*a*, and the upper tip 18 of hook portions 5 of the improved MV adapter 30 is nearly the same size as the side dimensions of the metal top 21 of the MV 13 that the improved MV adapter 30 of the present invention attaches to. The fairly close tolerances between these contacting surfaces provides a firm locking attachment of the improved MV adapter 30 to the standard MV 13.

The piercing spike 4, with its sharp pointed spike tip 9, is longer than resilient members 3 and 3*a*, with their attached foot pieces 12 and their hook portion 5, and guiding ramp portion 6. Because the sharp pointed spike tip 9 of the piercing spike 4 extends beyond the level of the resilient attachment limbs (3, 3*a*, 5 and 6), when the improved MV adapter 30 of the present invention is inserted into the rubber or elastomer stopper 20 exposed by the center hole 25 in the metal top 21 of the standard MV 13, the sharp pointed spike tip 9, of the piercing spike 4, engages and pierces the rubber or elastomer stopper 20 of the standard MV 13 first. This initial piercing of the rubber or elastomer stopper 20 by the leading spike tip 9 of the improved MV adapter 30 of the present invention stabilizes the improved MV adapter 30 onto the metal top 21 before the shorter diameter between the two hook portions 5 of the angled foot pieces 12 of the resilient attaching means 3 and 3*a* encounters the larger diameter 22 of the metal band 21 on the top rim of metal band 21 of the top of the standard MV 13.

When attaching the improved MV adapter 30 of the present invention to the standard MV 13, the MV adapter 30 will have the re-usable cover cap 14 attached to the syringe end 1. The improved MV adapter 30 of the present invention is held with the fingers holding onto the cover cap 14 and resting against the upper flat surface 28 of flange 2. As the fingers grip the cover cap 14 attached to syringe end 1, and push forward against the flat surface 28 of the flange 2, the sharp pointed spike tip 9 of the piercing spike 4 is placed at the exposed radial center of the self sealing rubber or elastomer stopper 20 of the standard MV 13. As the MV adapter 30 is pushed further forward, the sharp pointed spike tip 9 of the piercing spike 4 pierces the center of the self sealing rubber or elastomer stopper 20 of the top of the standard MV 13. The entry of the sharp pointed spike tip 9 of the piercing spike 4 into the rubber or elastomer sealing top 20 of the standard MV 13 stabilizes the improved MV adapter 30 in the center of the self sealing rubber or elastomer stopper 20 of the standard MV 13. This prevents any tendency for the MV adapter 30 of the present invention to slip around the metal top 21 of the standard MV 13 and become contaminated. As the spike 4 of the improved MV adapter 30 of the present invention is pushed further into the rubber stopper 20, the MV adapter 30 remains stabilized in the center of the rubber or elastomer stopper 20 of the standard MV 13, not tending to slip off to one side and contaminate sterility of the attaching components. With further pushing forward of the improved MV adapter 30 of the present invention into, and onto the standard MV 13, the inverted funnel shaped guiding ramp portions 6 of the angled foot piece 12 of the resilient attachment means 3 and 3*a* contact the diameter 22 of metal top 21 of the standard MV 13 and guide it straight, in the axial direction of the piercing spike 4.

The resilient attachment limbs 3 and 3*a* flex outward away from the upper corners 31 of the metal top 21 of the MV 13 because of the lateral vector force exerted on them by the pushing pressure from the outward angle of the guiding ramp portion 6 of the angled foot piece 12. This outward flexing of the resilient attachment limbs 3 and 3*a*, caused by the lateral vector force, continues as the improved MV adapter 30 of the present invention is pushed farther onto the MV 13, until the hook portions 5 of the angled foot pieces 12 are spread to a distance equal to the diameter 22 of the metal top 21 of the standard MV 13.

Further pushing forward of the improved MV adapter 30 of the present invention, with the spike end 4 advancing further into the rubber or elastomer stopper 20, with the hook portions 5 spread apart the distance equal to the diameter 22 of the metal top 21 of the standard MV 13, causes the upper tips 18 of hook portions 5 to resiliently slip beneath the lower edge of the metal cap 21, firmly grip, and thus permanently attach the improved MV adapter 30 of the present invention to the standard MV 13 with the upper tips 18 of the hook portion 5 of the angled foot pieces 12 firmly gripping the corner junctions 27 where the metal band 21 crimp meets the underside of glass mouth 19 near the neck 26.

Because the improved MV adapter 30 is initially fixed to the center of the rubber stopper 20 on the standard MV 13 by the leading piercing tip 9 of piercing spike 4, there is no slipping of the improved MV adapter 30 of the present invention on or around the metal top 21 of the standard MV 13 as the resilient attaching limbs 3 and 3*a* and angled foot pieces 12 with guiding ramp portions 6 flex outward, slip over, and lock onto the metal top 21 of the standard MV 13 by the hook portions 5 of the angled foot pieces 12. The initial fixation in the center of the rubber stopper 20 of the improved MV adapter 30 by the forward extending sharp pointed tip 9 of the piercing spike 4 combined with resultant lateral vector forces on the guiding ramps 6 of the angled foot pieces 12 attached to the resilient attachment limbs 3 and 3*a* guiding and pushing the hook portions 5 of the angled foot pieces 12 of the resilient attachment limbs 3 and 3*a* onto the sides and to the undersurface of the MV 13 produces an easy, safe, accurate and sterile method to permanently attach the improved MV adapter 30 of the present invention to a standard MV 13. Thus, when using the MV adapter 30 of the present invention, there is less chance of contaminating the MV adapter 30 itself, the rubber or elastomer stopper 20, the top of the standard MV 13, and the sterile medication contained inside of the standard MV 13. This represents an easier, safer, more accurate, and more sterile method of attaching a MV adapter to a standard medication vial 13.

Because the distance between the hook portions 5 of the angled foot pieces 12 at the ends of resilient attachment limbs 3 and 3*a*, of the improved MV adapter 30 is shorter than the diameter 22 of the metal top 21 of the standard MV 13 that it is to be attached to, without the presence of the outward extending guiding ramp portions 6 of the angled foot pieces 12 it will be difficult to attach such a MV adapter (such as with Holtz, Curley et al., and Forman et al.) to the standard MV 13. An adapter without the inverted funnel design of the guiding ramp portions 6 of the angled foot pieces 12, or the initial stabilization feature provided by the leading piercing spike end 4 with its sharp pointed spike tip 9 being longer than the resilient attachment limbs 3 and 3*a*, will tend to slip to one side or slide around the top of the standard MV 13 as one attempts to attach and affix it permanently to a standard MV 13. This instability and slipping can result in loss of sterility of the joining parts, from finger contamination or rubbing against a non-sterile portion of the standard MV 13.

Because the sharp pointed tip 9 of the spike 4 has a symmetrical conical shape instead of a slanted angular tip as in piercing needles of much of the prior art, it is easier to insert the spike 4 in the center of the rubber or elastomer sealing stopper 20 and push the spike 4 straight through without it wandering off center. Also, because the spike bore 7 communicates with the inside of the standard MV 13 through the side hole(s) 8, there is no tendency for the spike to core or cut off a piece of the rubber or elastomer stopper 20 as it is being inserted into the standard MV 13 as may occur with the angular end bore design of piercing needles of much of the prior art. A dislodged piece of the rubber or elastomer stopper 20 may clog the needle, drop into and contaminate the medicine inside the MV 13, or worse yet, get drawn with the medicine, into the syringe 15 and then be injected into the blood stream of a patient.

The distance between the farthest ends of the guiding ramp portions 6 of the angled foot piece 12 of the end of resilient attachment limbs 3 and 3*a* is substantially greater than the diameter 22 of the metal top 21 of the standard MV 13 to which the improved MV adapter of the present invention 30 is being attached to. Guiding ramp portion 6 of each angled foot piece 12 is angled upward and points inward like sides of an inverted funnel. When the upward and inward angled foot pieces 12 with the guiding ramp portions 6 and the hook portions 5 are lowered over the smaller diameter 22 of the metal top 21, the inverted funnel-shaped guiding ramp portions 6 cover beyond the full diameter 22 of the MV 13 and guide the hook portions 5 over the metal top 21 to permit them to permanently attach and lock the improved MV adapter 30 of the present invention onto the MV 13. The lateral vector force resulting from the downward push on the angled foot pieces 12 pushes the hook portions 5 outward. The downward vector force pushes the hook portions 5 downwards past the upper outer corner 31 of the metal top 21, down the sides of the metal top 21 of the standard MV 13, and then past the lower outer corner 32 of the metal top 21. The resilient members 3 and 3*a* bring the hook portions 5 and their upper tip portions 18 back, under and into the lower inner corner 27 of the top of the MV 13, where the metal top 21 of the standard MV 13 ends at the glass neck 26 of the standard MV 13. The hook portions 5 now permanently lock the improved MV adapter 30 of the present invention onto the standard MV 13 below the metal top 21 at the point 27 near the point where the lower inner end of the metal top 21 and the glass neck 26 approach each other.

The final location of the hook portions 5 at the point 27 below the metal top 21 of the standard MV 13 makes a permanent attachment to the standard MV 13, the resiliency of the attachment limbs 3 and 3*a* prevents the improved MV adapter of the present invention from coming off of the attached standard MV 13 when the medication filled syringe 15 is pulled off. The permanent attachment of the improved MV adapter 30 of the present invention to the standard MV 13, permits faster and more efficient filling of syringes 15 without the use of needles, and it helps preserve sterility of both the improved adapter of the present invention 30 and sterility of the contents of the medication vial 13. In contrast to using a MV adapter that does not have permanent attachment means (Smith et al., Froning et al.), when using the improved MV adapter of the present invention 30, one does not have to make a special effort to hold the improved MV adapter 30 at the top surface 28 of the flange 2 and simultaneously hold lower surface 17 of the flange 2 against the top surface of the metal top 21 of the standard MV 13 in order to prevent the MV adapter from being pulled off with the syringe 15 when the medication filled syringe 15 is pulled of. The resilient attachment means 3 and 3*a* will hold the improved MV adapter 30 of the present invention onto the standard MV 13. One may now hold the standard MV 13 at any convenient location when pulling the medication filled syringe off of the improved MV adapter of the present invention 30 without having concern that it will come off of the standard MV 13 and become contaminated. In the case of an adapter without attachment means, if the adapter comes off with the syringe 15, and it is subsequently pushed back onto the standard MV 13, loss of sterility of both the MV adapter and the contents of the medication vial can occur.

The unique combination of the sharp pointed tip 9 of the piercing spike 4 of the improved MV adapter 30 of the present invention being longer, or extending further forward, than the resilient attachment limbs 3 and 3*a*, the resiliency of the attachment limbs 3 and 3*a*, and the design of the resilient attachment limbs 3 and 3*a* with their metal-top-encompassing angled foot pieces 12 with their guiding ramp portions 6 and their hook portions 5, permits the improved MV adapter 30 of the present invention to be attached to a standard MV 13 in a manner which is easier, more accurate, safer, and more sterile. Once the improved MV adapter 30 of the present invention has been permanently attached to the standard MV by this improved attachment method, it permits filling standard syringes 15 without the use of needles, with sterile medication from a standard MV 13, in a manner which is easier, faster, more efficient, and most importantly, more sterile.

It is to be understood that the present invention is not limited to the sole embodiments described above, but encompasses any and all variations falling within the scope of the appended claims.

We claim:

1. An adapter device for withdrawing medication from a medicine vial into a syringe without the use of a needle, the medicine vial having a permanently affixed elastomer cap having a diameter and a thickness, the syringe having an inlet, the adapter device comprising:
   - a body;
   - detachable means for sealably receiving the inlet of the syringe, said means being substantially centered on said body and having a central bore fluidically connecting said adapter device with the syringe;

means for sealably piercing the cap of the medicine vial, said piercing means extending substantially perpendicular to said body and opposite said detachable means, being substantially elongated in shape, having a longitudinal axis with a spike bore extending along the longitudinal axis fluidically connected to the central bore and having an adapter inlet, fluidically connected to the spike bore, positioned along the longitudinal axis at a distance between the inlet and said body greater than the thickness of the cap;

at least two resilient attachment limbs extending from said body substantially in the same direction as said piercing means, separated from one another by a distance equal substantially to the diameter of the cap, each of said limbs having a length less than that of said piercing means and equal substantially to the thickness of the cap; and angled guiding foot members attached to the distal ends of each of said limbs, each of said foot members having guiding means and locking means with the locking means extending inward from said limbs towards the piercing means and towards the detachable receiving means with said locking means separated from one another by a distance less than the diameter of the cap and with the guiding means extending outward from said limbs away from the piercing means and away from the detachable receiving means, with said guiding means separated from one another by a distance greater than the diameter of the cap.

2. The adapter device recited in claim 1, further comprising a cap for removably covering said receiving means.

3. The adapter device recited in claim 1, wherein said detachable receiving means further includes luer fitting means for releasably securing the inlet of the syringe to said receiving means.

4. The adapter device recited in claim 1, wherein said piercing means is a spike.

* * * * *